(12) United States Patent
Bassi

(10) Patent No.: US 7,985,600 B2
(45) Date of Patent: Jul. 26, 2011

(54) USE OF PERFLUOROPOLYMERS IN THE DETERMINATION OF THE RECEPTOR-LIGAND BINDING CONSTANT

(75) Inventor: Mattia Bassi, Milan (IT)

(73) Assignee: Solvay Solexis S.p.A., Milan (IT)

( * ) Notice: Subject to any disclaimer, the term of this patent is extended or adjusted under 35 U.S.C. 154(b) by 0 days.

(21) Appl. No.: 12/293,149

(22) PCT Filed: Mar. 14, 2007

(86) PCT No.: PCT/EP2007/052390
§ 371 (c)(1),
(2), (4) Date: Sep. 16, 2008

(87) PCT Pub. No.: WO2007/104773
PCT Pub. Date: Sep. 20, 2007

(65) Prior Publication Data
US 2009/0042316 A1 Feb. 12, 2009

(30) Foreign Application Priority Data
Mar. 16, 2006 (IT) .............................. MI2006A0480

(51) Int. Cl.
*G01N 33/544* (2006.01)
*G01N 33/53* (2006.01)
*G01N 33/547* (2006.01)

(52) U.S. Cl. ......... 436/528; 435/7.5; 435/7.92; 436/532

(58) Field of Classification Search ........................ None
See application file for complete search history.

(56) References Cited

U.S. PATENT DOCUMENTS

| | | | |
|---|---|---|---|
| 4,485,250 A * | 11/1984 | Squire .......................... | 549/455 |
| 4,703,018 A | 10/1987 | Craig et al. | |
| 4,745,165 A | 5/1988 | Arcella et al. | |
| 4,789,717 A | 12/1988 | Giannetti et al. | |
| 4,864,006 A | 9/1989 | Giannetti et al. | |
| 4,910,276 A | 3/1990 | Nakamura et al. | |
| 5,079,155 A * | 1/1992 | Cox et al. ...................... | 435/181 |
| 5,152,287 A | 10/1992 | Kane | |
| 5,173,553 A | 12/1992 | Albano et al. | |
| 5,266,498 A * | 11/1993 | Tarcha et al. ................. | 436/525 |
| 5,270,193 A * | 12/1993 | Eveleigh ....................... | 435/181 |
| 5,313,264 A | 5/1994 | Ivarsson et al. | |
| 5,374,563 A | 12/1994 | Maule | |
| 5,585,449 A | 12/1996 | Arcella et al. | |
| 5,690,907 A | 11/1997 | Lanza et al. | |
| 5,939,021 A | 8/1999 | Hansen et al. | |
| 6,180,415 B1 | 1/2001 | Schultz et al. | |
| 6,297,334 B1 | 10/2001 | Marchese et al. | |
| 6,413,786 B1 | 7/2002 | Hansen et al. | |
| 2001/0023077 A1 | 9/2001 | Erb et al. | |
| 2003/0017078 A1 | 1/2003 | Trapp et al. | |
| 2004/0014060 A1 | 1/2004 | Hoheisel et al. | |
| 2004/0115823 A1 | 6/2004 | Potyrailo | |
| 2004/0253744 A1 | 12/2004 | Rife et al. | |

FOREIGN PATENT DOCUMENTS

| | | |
|---|---|---|
| DE | 19938369 | 3/2001 |
| EP | 0 633 257 B1 | 4/1997 |
| EP | 0 250 766 B1 | 9/1999 |
| EP | 1300684 | 4/2003 |
| WO | WO 00/48023 A1 | 8/2000 |
| WO | WO 2006/032419 A1 | 3/2006 |

OTHER PUBLICATIONS

Angew. Chem. Int. Ed. 1998, 37, p. 2785.
Hamola et al., "*Surface Plasmon Resonance Sensors: review*", Sensors and Actuators B 54, 1999, p. 3-15.
Schuck., "*Use of surface plasmon resonance to probe the equilibrium and dynamic aspects of interactions between biological micromolecules*", Annu. Rev. Biophys. Biomol. Struct., 1997, 26, pp. 541-566.
Giannetti et al., "*Polymerization of fluorinated monomers in perfluoropolyether microemulsions*", Richmac Magazine, La Chimica e l'Industria, 1997, pp. 22-29.

* cited by examiner

*Primary Examiner* — Shafiqul Haq
(74) *Attorney, Agent, or Firm* — Arnet Fox LLP

(57) ABSTRACT

Use of flat surfaces comprising perfluorinated polymers in the determination of the binding constant of two interacting molecular species by using measurements of reflected light intensity, said surface comprising at least one molecule with the receptor function adsorbed or immobilized on said surface, and at least one ligand which interacts with the receptor.

13 Claims, 5 Drawing Sheets

USE OF PERFLUOROPOLYMERS IN THE DETERMINATION OF THE RECEPTOR-LIGAND BINDING CONSTANT

CROSS-REFERENCE TO RELATED APPLICATION

This application is a National Stage entry of International Application No. PCT/EP2007/052390, filed Mar. 14, 2007, the entire specification and claims of which are incorporated herewith by reference.

The present invention relates to a simple and efficient method for the quantitative determination of ligand interactions with adsorbed or immobilized receptors on the surface of a polymer by direct measurement of the reflected light intensity.

More specifically, the present invention refers to the determination of ligand interactions with receptors wherein planar surfaces of perfluorinated polymeric materials are used.

Several various methods to determine interactions between ligands and receptors, that is the binding affinities of ligand-receptor reversible systems, of chemical, biochemical or biological interest have been reported in the prior art. A list is reported in Angew. Chem. Int. Ed. 1998, 37, page 2785. These known methods generally comprise the receptor immobilization on a suitable flat surface and the direct or indirect measurement of the variations of certain surface properties, for example the optical ones, after the ligands are contacted with the surface. The variations are due to the formation of receptor/ligand couples.

One class of these methods requires the labelling of the ligand in solution, that is the covalent modification of the ligand with fluorescent, luminescent or radioactive species. See for example patent application US 2004/0014,060. However it is to be noted that this technique is very complex and long and difficult to be used in screening tests where numerous different ligands are used. Furthermore it is required a washing out of the free ligands, that is those not interacted with the receptors, as they interfere with the measurement. A further drawback resides in the fact that the labelling can influence the ligand-receptor interaction.

Another class of methods for the determination of the receptor-ligand interactions, for example those occurring on a cell membrane surface, utilizes the variations induced on a surface by the bond formation in the receptor-ligand couple, without labelling the ligand. An example of this method uses the biosensor BIAcore, marketed by GE Healthcare (Uppsala, Sweden). See for example U.S. Pat. No. 5,313,264 and U.S. Pat. No. 5,374,563. In the biosensor, wherein the principle of Surface Plasmon Resonance (SPR) is used (see the publication Jiri Homola, Sinclair S. Yee, Gunter Gauglitz, Surface plasmon resonance sensors: review, Sensors and Actuators B, vol. 54 (1999), pages 3-15), an evanescent optical wave couples with surface plasmons of thin layers (50 nm) of conducting materials as silver or gold, and generates a resonance phenomenon at specific angles. This allows to determine the variation of the refractive index of the layers of immobilized substance on the metal, for example a ligand-receptor couple. The binding constants between ligand and receptor are obtained from this variation. Even though it is in practice very used, this method is rather complicated and expensive and it is not always accurate in the determination of the binding constants. See for example the publication "Use of surface plasmon resonance to probe the equilibrium and dynamic aspects of interactions between biological macromolecules", by Peter Schuck, Annu. Rev. Biophys. Biomol. Struct., 1997, 26, pages 541-566. In fact, the method is based on the detection of the coupling angle of a laser beam determined by the adsorbed mass. Indeed the adsorbed mass influences the plasmon propagation rate on a metal layer which changes the intensity of the evanescent wave and thus the coupling angle of the laser beam. The problems connected to the use of the BIAcore method mostly depend on the complexity of the method:

the measured signal depends on the physical properties of five different products through a complicated functional dependence including parameters not known a priori. The parameters are: the glass support or similar products, the thin layer of the conductor on the support, the polymeric layer, the molecules adhering on the latter and the aqueous solution;

the sensitivity and accuracy of the measurement depend on the thickness and surface quality of the conductor layer forming the sensor. See the publication "Optical properties and instrumental performances of thin gold films near the surface plasmon resonance" by H. Neff et al., Thin solid films, 2006, 496, pages 688-697;

the measurements are based on the detection of the light intensity at various angles and this requires an equipment capable of high resolution angular scannings and composed by high precision moving parts or photodetector matrices of suitable space resolution. See the article "Quantitative interpretation of the response of surface plasmon resonance sensors to adsorbed films" by L. S. Jung et al, Langmuir, 1998, 14, pages 5636-5648.

Said problems arise:

in the non agreement between the affinity constant values determined through the binding kinetics and those obtained at the thermodynamic equilibrium;

in the impossibility to forecast the intensity of the signal generated when receptor/ligand couples are formed on the surface. As a matter of fact the signal depends on not previously known parameters.

The need was therefore felt to have available a simple method for the determination of the interactions between ligands and receptors overcoming the prior art drawbacks.

It has now been unexpectedly and surprisingly found that this is possible by using a quantitative optical method allowing the determination of binding affinities of molecular species by means of the method described hereinafter.

Figure 1:
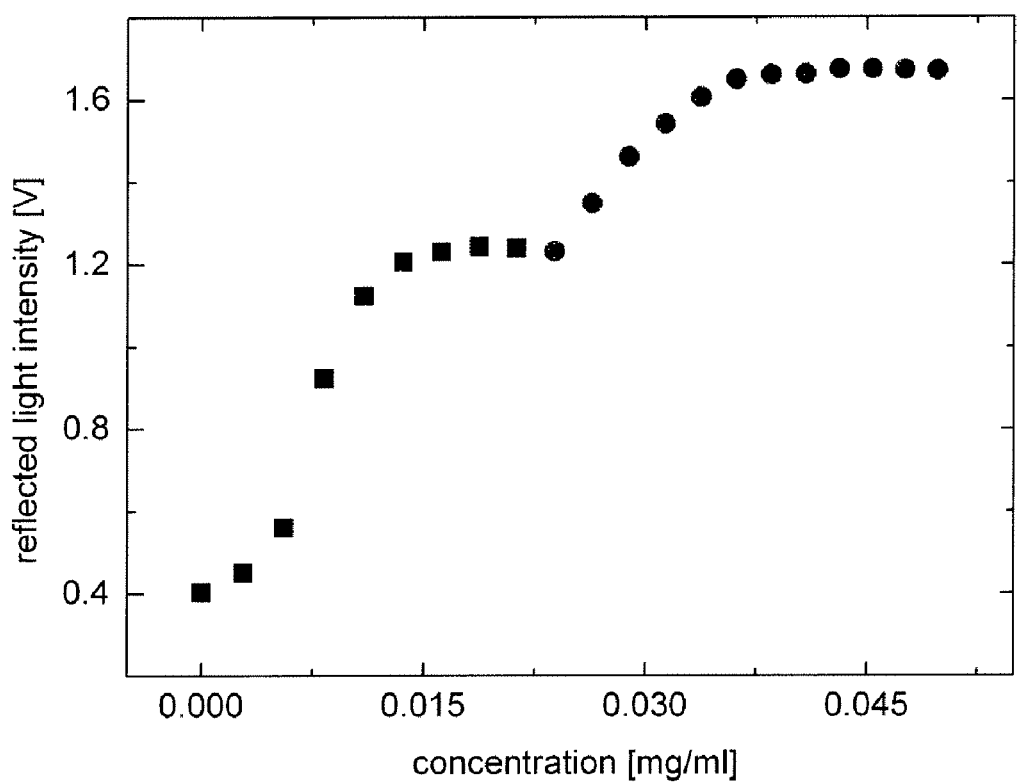
FIG. 1 is a graph depicting the intensity of reflected light [V] as a function of concentration [mg/ml] of the solutions described in Example 1a) (O) and 1b) (M).

An object of the present invention is the use of a flat surface comprising perfluorinated polymers in the determination of the binding constant of two interacting molecular species and of the concentration of a ligand in solution by using the measurements of the reflected light intensity, the surface comprising at least a perfluorinated polymer, at least one receptor molecule adsorbed on it or chemically bound, and at least one ligand molecule interacting with the receptor.

Preferably the flat surfaces are substantially formed of perfluorinated polymers.

More specifically, the measurements comprise the following steps:

(a) a surface of the perfluorinated, semicrystalline or amorphous polymer, preferably amorphous, is brought into contact with an aqueous solution containing from 1 nanogram/ml to 10 milligram/ml in concentration of molecules with a function of receptor such as antibodies, or other proteic or peptidic complexes or nucleic acids or lipids or amphiphilic surfactants or block polymers ended with a receptor, optionally mixed with other molecules (intercalating) having no receptor function, optionally measuring during each addition the light intensity reflected from the interface between the aqueous solution and the polymeric surface and reporting the measured value on a diagram in function of the time or in function of the receptor concentration progressively additioned, optionally repeating this procedure by bringing the surface into contact with other aqueous or non-aqueous solutions of the said molecules;

(b) addition to the solution obtained in step (a) of a sequence of known volumes of an aqueous solution of a ligand having a known concentration, measuring during each addition the light intensity reflected from the interface between the aqueous solution and the polymeric material and reporting the measured value on a diagram in function of the time or in function of ligand concentration $[T_0]$ progressively additioned, and fitting the reflected light intensity data I in function of the ligand additions with the formula:

$$I = cI_0(R^\perp \sin^2 v + R^\| \cos^2 v) + I_N \quad (1)$$

wherein $I_0$ represents the incident light intensity on the interface, c is a factor taking into account the possible surface roughness and is 1 in case of a flat surface, $I_N$ is the light intensity measured by the detector in the absence of the polymer, v is the angle formed by the light polarization direction with the incidence plane, $R^\perp$ and $R^\|$ are the reflection coefficients drawn from the Fresnel formulas for a thin layer respectively in case of polarization perpendicular and parallel to the incidence plane and depend on the ligand amount in contact with the receptors adsorbed on the interface, from which the ligand concentration $[T_L]$ interacting with the receptors on the surface, and, optionally by means of the Langmuir absorption formula, the K constant of receptor-ligand binding are obtained.

The Fresnel formulae for the thin layer are those, for example, described in F. L. Pedrotti, L. S. Pedrotti, "Introduction to Optics", Prentice Hall, New Jersey, 1993, pages 393-395; R. D. Guenther, "Modern Optics", John Wiley & Sons, pages 67-83.

In fact the ligand amount bound to the receptor as a function of the ligand additions is expressed by a function known as "Langmuir isotherm", which depends on the receptor concentration and on the affinity constant (binding constant). For the Langmuir isotherm see, for example, Paul C. Hiemenez, "Principles of Colloid and Surface Chemistry", Marcel Dekker, New York, 1997, pages 287-298.

The volume of receptors and ligands absorbed or immobilized on the surface of the reflected light values is obtained by following the Fresnel formulas for the thin layer reflection, the reflected light intensity increases with the amount of the adsorbed or immobilised receptor and of the amount of interacting ligand with a function depending on the refractive indexes of water, polymeric substrate and molecules on the surface, as well as on the receptor and ligand surface concentration and on the affinity constant.

The method of the present invention is applicable for any incidence angle and any light polarization. Moreover according to formula (1) the method is applicable for transparent or turbid and/or absorbing solutions.

The ratio between the variation of the light intensity due to the molecular layers on the surface and the light intensity measured before carrying out step (a) or step (b) can be varied to improve the method sensitivity either modifying the incidence angle and/or the light collection angle, or by changing the polarization of the incident light and/or measuring the polarization variations of the detected light.

For example, under the following conditions:
light incidence angle of 45°,
polarization perpendicular to the incidence plane (v=90°),
difference between the refractive indexes of the aqueous solution and of the polymeric substratum (Δn) lower than or equal to 0.012, the refractive index of the receptor equal to the refractive index of the ligand;
thickness of the molecular layer of adsorbed or immobilized receptors and interacting ligands lower than 15 nm, the reflected intensity I can be determined according to the following formula (2) approximated with an error lower than 1% with respect to the equation (1):

$$I = 2I_0 \left(\frac{\pi V N_a}{\lambda A}\right)^2 \frac{(n_a^2 - n_0^2)(n_a^2 n_0^2 - n_0^4 + 2n_a^2 \Delta n)}{n_0^4} \left(\frac{m_R[T_R]}{\rho_R} + \frac{m_L[T_L]}{\rho_L}\right)^2 + I_b$$

wherein $I_0$, $[T_L]$, Δn are as above defined, $[T_R]$ is the concentration of receptors absorbed or immobilized on the surface, $n_a$ is the refractive index of the ligand and of the receptor, $m_L$, $\rho_L$ represent the molecular weight and the density of the ligand respectively, $m_R$, $\rho_R$ represent the molecular weight and the density of the receptor respectively, V is the volume of the aqueous solution, A is the area of the polymeric material surface on which the receptor and ligand interaction takes place, λ the wave length of the incident light, $n_0$ is the refractive index of the aqueous solution, $I_b$ the intensity measured before the addition of receptors (before step (a)).

The concentration $[T_L]$ of ligand stuck on the surface in a state of thermodynamic equilibrium can be expressed by the Langmuir absorption formula (3)

$$[T_L] = [T_0] + K^{-1} + [S_0] - \sqrt{([T_0] + K^{-1} + [S_0])^2 - 4[T_0][S_0]} \quad (3)$$

wherein $[T_0]$ is as above defined, $[S_0]$ is the molar concentration of receptor-ligand binding sites, and K is the affinity constant (also said binding constant).

The other parameters being known, fitting the equation (2) to the measured values of reflected intensity, the concentration $[S_0]$ of receptors adsorbed on the surface and the affinity constant K for the ligand-receptor interaction are obtained.

As said the known parameters, i.e. parameters measurable or already known, are characteristic of the ligand-receptor couple, once the couple is defined.

The perfluoropolymers used for the surface can be semicrystalline or amorphous. The surface perfluoropolymers are selected, for example, from:
1) tetrafluoroethylene homopolymer (PTFE), or semi-crystalline copolymers of tetrafluoroethylene (TFE);
2) amorphous copolymers of TFE;
3) amorphous homopolymers of perfluorinated dioxole rings.

Preferably the perfluoropolymers used in the present method are selected from:
1) semicrystalline tetrafluoroethylene (TFE) copolymers containing from 0.5% up to about 10% by moles, the maximum limit being such that the copolymer is semicrystalline, of one or more fluorinated comonomers, such as, for example, perfluoroalkylvinylethers (PAVE), preferably selected from perfluoromethylvinylether, perfluoroethylvinylether, perfluoropropylvinylether; perfluorodioxoles; hexafluoropropene (HFP);
2) amorphous copolymers of TFE with other fluorinated monomers, such as for example perfluoroalkylvinylethers (PAVE), perfluorodioxoles of formula

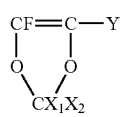 (I)

wherein
Y is equal to F or to $OR_f$ wherein $R_f$ is a perfluoroalkyl having from 1 to 5 carbon atoms; preferably Y is equal to $OR_f$; $X_1$ and $X_2$, equal to or different from each other, are —F or —$CF_3$; preferably in formula (I) $X_1$, $X_2$ are —F; $R_f$ is preferably —$CF_3$, —$C_2F_5$ or —$C_3F_7$; more preferably the fluorodioxoles of formula (I) are those wherein Y is equal to $OR_f$ wherein $R_f$ is —$CF_3$ and $X_1$, $X_2$ are —F (that is 2,2,4-trifluoro-5-trifluoromethoxy-1,3-dioxole (TTD)) (see, for example, EP 633,257); hexafluoropropene (HFP); perfluorooxyalkyl vinylethers, optionally containing "cure-site" monomers containing bromine or iodine atoms (see, for example, U.S. Pat. No. 4,745,165) or iodine or bromine atoms in end position in the polymeric chain (see, for example, U.S. Pat. No. 5,173,553); bis-olefins having general formula:

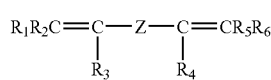 (II)

wherein:
$R_1, R_2, R_3, R_4, R_5, R_6$, equal to or different from each other, are H or $C_1$-$C_5$ alkyls, Z is a linear or branched $C_1$-$C_{18}$ alkylene or cycloalkylene radical, optionally containing oxygen atoms, preferably at least partially fluorinated, or a (per)fluoropolyoxyalkylene radical (see for example U.S. Pat. No. 5,585,449);

3) amorphous homopolymers of a perfluorodioxole of formula (I) as above defined.

In class 2), instead of the perfluorodioxole of formula (I), diene monomers containing oxygen atoms can be used. These comonomers cyclize during the polymerization giving dioxolane rings. See, for example, U.S. Pat. No. 4,910,276. In particular the following comonomers can be mentioned:

$CF_2$=$CFOCF_2CF$=$CF_2$, $CF_2$=$CFOCF_2CF_2CF$=$CF_2$, $CF_2$=$CFOCF_2OCF_2CF$=$CF_2$, $CF_2$=$CFO(CF_2)_2CF$=$CF_2CF_3$, $CF_2$=$CFOCF_2CF(CF$=$CF_2)CF_2CF$=$CF_2$.

More preferably the perfluoropolymer is an amorphous perfluoropolymer.

Preferably the perfluorinated polymers of classes 2) and 3) are used. In particular amorphous copolymers of TFE containing from 20% to 80% by moles of perfluorodioxole of formula (I), preferably containing TTD. An amount from 20% to 60% by moles of TTD is preferred.

The polymers of present invention can be obtained with various methods of the prior art, for example by coagulating aqueous latexes containing perfluoropolymer particles obtained by polymerization in aqueous emulsion, preferably in the presence of a (per)fluoropolyoxyalkylene microemulsion. See, for example, U.S. Pat. No. 4,864,006, U.S. Pat. No. 4,789,717, EP 250,766, U.S. Pat. No. 6,297,334 and in the publication "Polymerization of fluorinated monomers in perfluoropolyether microemulsion", Giannetti E., Chittofrati A., Sanguineti A., La chimica e l'industria, October 1997, RICHMAC Magazine, herein incorporated by reference.

The polymeric surface can be included in a cell with or without the possibility of flowing the solution, or it can be included in an immersion or portable probe. The polymeric surface can be a face of a prism or sheet or plaques with parallel or non parallel faces, or films with thickness preferably higher than 1 micron. The polymeric manufactured article can be obtained by known techniques such as molding, extrusion, film formation through casting, spin-coating, dip-coating, etc. The polymeric surface can be smooth or can present a regular or irregular roughness. The surface roughness of the films can be controlled during the film formation, for example by suitably selecting solvents and evaporation temperatures or annealing. Another method consists of lapping, imprinting operations, or use of solvents over a surface already formed, or by the annealing of films at selected temperature for selected time. The roughness can produce a component of diffused light which however is not a disadvantage of the present method, as it is proportional to the molecular layers covering the surface like the reflected light. In this case it is possible to measure the light intensity even in a different direction from that of the geometrical reflection.

The receptor used are those generating a monolayer adsorbed or immobilized on the solid surface. The adsorption can be due to the hydrophobic or electrostatic interactions of the receptor molecules with the surface.

The immobilization can be obtained by direct absorption of the receptor molecule on the surface as well as the formation of chemical bonds between the receptor molecules and the polymeric surface or other compounds bound or absorbed to the polymeric surface, for example through coating. The receptor molecules can be immobilized and/or chemically modified through methods of the prior art, such as chemical methods or electromagnetic irradiation or plasma treatment.

The molecules or the molecular complexes with the function of ligands, after their immobilization to the surface through the interaction with the receptors, can at their turn play the function of receptor for other molecules or molecular complexes interacting with them. As said, the receptors can be surfactants, for example the non ionic amphiphilic. These generate a self assembled monolayer on the surface. The formation of the monolayer can be determined by carrying out step (a) of the present method and observing the achievement of an asymptotic value of the reflected light as a function of the receptor concentration progressively added.

The receptor molecules, as said, can be used in admixture with molecules without receptor function (intercalating molecules). The latter can generally be selected between surfactants, proteins, etc., and must not show specific interactions with the ligand to be analyzed. The absence of said interaction can be determined by carrying out step (a) of the method according to the invention by using only the intercalating molecules and then step (b). In this case no variations of the reflected light intensity has to be observed during step (b).

The surfactants, either bringing a receptor function or used as intercalating molecules, can be selected among non-ionic surfactants, such as for example glycolipids, polyoxyethylenes, polyoxypropylenes or alkyl-glycoxides, or among ionic surfactants, for example anionic surfactants such as sodium bis(2-ethylhexyl)sulphosuccinate (AOT), or cationic such as didodecyl-dimethylammonium bromide (DDAB).

The surfactants used as receptors are prepared by reacting the surfactants with a receptors according to known processes of the prior art.

The receptor-ligand couple is defined as a couple of molecules, for example proteins, nucleic acids, glycoproteins, carbohydrates, hormones, having an affinity capable of forming a more or less stable bond. In particular antibody/antigen, enzyme/inhibitor, carbohydrate/carbohydrate, protein/DNA, DNA/DNA, peptide/peptide can be mentioned.

In steps (a) and (b), the measurements of the reflected light intensities are carried out by detecting the intensity of the reflected light, as a function of time, until reaching a constant value. It has been found that the time necessary for reaching the constant value corresponding to the thermodynamic equilibrium depends on the type of receptor-ligand couple. Therefore the measurements allow the evaluation of the absorption-desorption kinetics.

The method of the present invention allows to detect also small amounts of ligand down to 100 picograms (1 picogram=$10^{-12}$ g) of ligand on a surface of 1 mm$^2$ corresponding to the sensitivity limit of the order of the most sensitive techniques of the prior art. The measurement surface area is defined as the surface on which the receptor is absorbed or immobilized. This area can be reduced to a size of a few hundred squared microns, thus allowing the detection of a few picograms of ligand. The whole polymeric surface can host several various measurement surface area.

As said, it is surprising and unexpected that the analysis of the reflected light from a surface is effective in identifying and measuring directly, through the measurement of the reflected light intensity, the interactions between receptors and ligands.

Some Examples follow with illustrative but not limitative purposes of the present invention.

EXAMPLES

Example 1

Measurement of the Binding Constant Between the Protein Bovine Serum Albumin Conjugated with Biotin (BSA Biotinylated, Ligand) and Avidin (Receptor)

Step (a)

A right prism of a copolymer of TFE containing 60% by moles of perfluorodioxole TTD, obtained by mechanical working of a compression molded article, having 3 cm side and smooth surface mechanically worked by lapping, was dipped in 1.5 milliliters of water.

A light beam coming from a 5 milliwatt laser He—Ne is impinging perpendicularly on the right prism face not in contact with the aqueous solution. The reflection takes place at the interface between the longer side of the prism and the aqueous solution put into contact with it. The reflected beam comes out from the second smaller side of the prism and is detected by an amplified photodiode converting the reflected light intensity into an electric signal.

A 0.02 millimolar aqueous solution of protein Avidin (commercialized by Aldrich, cas. No. 1405-69-2) is added to the water, in 4 microliter portion each, for a total of 20 microliters. The solution is constantly kept under stirring.

After each addition the intensity of the light reflected from the prism face was measured for 2 minutes. The measured intensity reaches a constant value after about 1 minute and the constant values are reported in a diagram as a function of the concentration of Avidin, expressed in mg/ml, obtaining the curve reported hereinafter.

The progressive covering of the face dipped in the solution by the added protein is observable from the variation of the light intensity measured by the photodiode.

The complete covering is clearly shown by the achievement of an asymptotic value of the measured light intensity.
Step (b)

To the solution obtained in (a) where the prism is dipped, after the achievement of the asymptotic value, a 5 micromolar aqueous solution of Bovine Serum Albumin conjugated with biotin (marketed by Pierce, prod. No. 29130), is added at 20 microliter portion each. The solution is constantly kept under stirring. After each addition the reflected light intensity is measured as in step (a).

The measured intensity values are reported in a diagram as a function of the concentration of proteins and added to the curve represented by a diagram in step (a).

The formation of the BSA-biotin-Avidin bonds is shown by from the increase of the light intensity measured until the achievement of an asymptotic value indicating saturation of the Avidin binding sites with biotin.

By fitting to the reflected light intensity data as a function of the BSA-biotin concentration with formula (2), the receptor-ligand binding constant is obtained. The binding constant obtained is $2.6 \times 10^9$ liters$\times$moles$^{-1}$.

Example 2

The Example 1 was repeated but replacing the prism with a thin film of the same copolymer used in the Example 1. The film is obtained by casting and has a thickness of 17 micrometers. The film was mounted in a plexiglass square frame having a length of 1.4 cm and internal side of 0.4 cm.

On said film a laser light beam was impinging as in the Example 1, with an angle of 45° on the film surface. An amplified photodiode, placed at 90° with the direction of the light coming out from the laser, converts the light intensity into an electric signal. All the operations described in the Example 1 are then repeated obtaining a binding constant of $3.7 \times 10^9$ liters×moles$^{-1}$.

Example 3

Measurement of the Interaction Between Avidin (Receptor) and Bovine Serum Albumin Conjugated with Biotin (Iodinated BSA, Ligand) in a Solution with High Extinction Coefficient The measurement system of example 1 has been used. The prism is dipped in 1.5 mL of water, and a volume of 10 microliters of aqueous solution containing 10 micrograms of Avidin is added, while stirring the solution.

Figure 2:
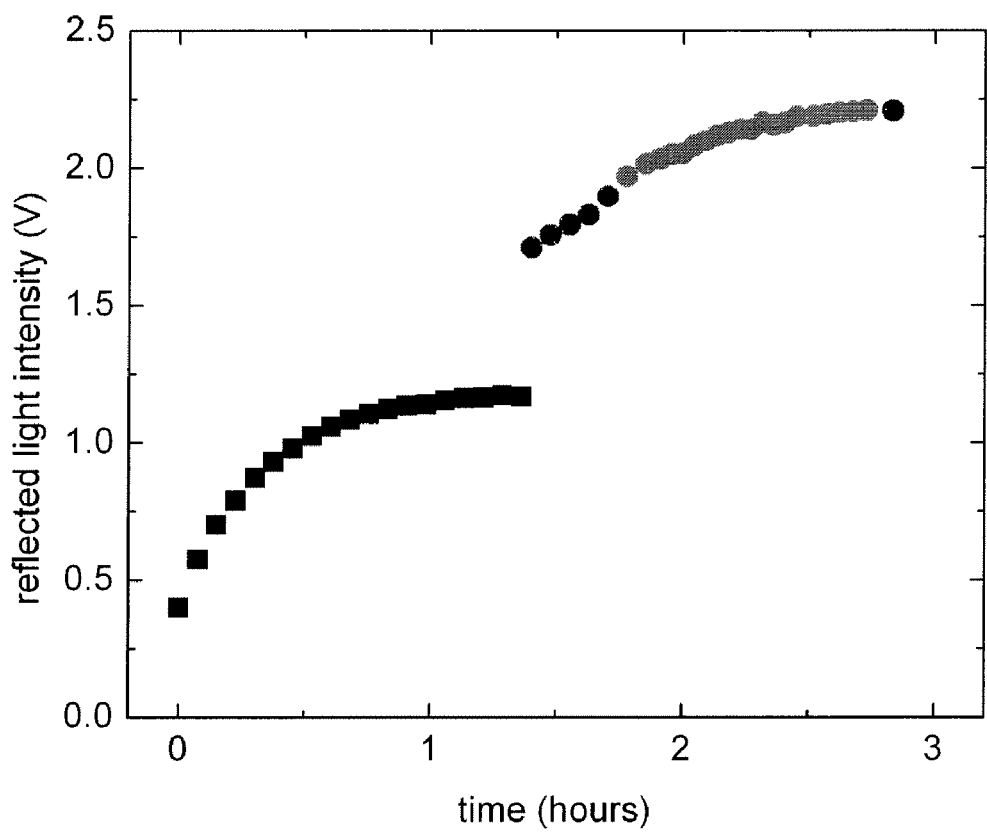
FIG. 2 is a graph depicting the intensity of reflected light (V) as a function of time (hours) of the solutions described in Example 3.

The intensity of the light reflected from the prism face is measured at regular intervals of 2 minutes and the measured intensity values (squares in FIG. 2) are reported in a diagram as a function of time obtaining the curve reported hereinafter.

To the solution, continuously stirred, is added a volume of 100 microliters of a colloidal suspension containing a volume fraction of 0.1% of sub-micron sized particles of iron oxide, which confer to the solution an extinction coefficient of 5 cm$^{-1}$, that is a value higher than the one reported for the whole blood at the wavelength of 633 nm.

The intensity of the reflected light measured by the photo diode rapidly increases by nearly 50% after the addition of the colloidal suspension.

After two minutes, a volume of 10 microliters of a aqueous solution containing 10 micrograms of biotinylated BSA is added. The intensity of the light reflected by the prism face is measured at regular intervals of two minutes, and the measured intensity values (represented as dots in FIG. 2) are reported in a diagram as a function of time, obtaining the curve reported hereinafter.

The increase of the voltage generated by the photodiode after the achievement of the asymptotic value associated with the saturation of the binding sites is about 0.5 volt, very close to the increase measured in Example 1 in a transparent solution without the addition of the turbid suspension.

Thus, the presence of a absorbing and scattering medium doesn't affect sensibly the measurement of the interaction between Avidin and biotinylated BSA.

Example 4

Figure 3:
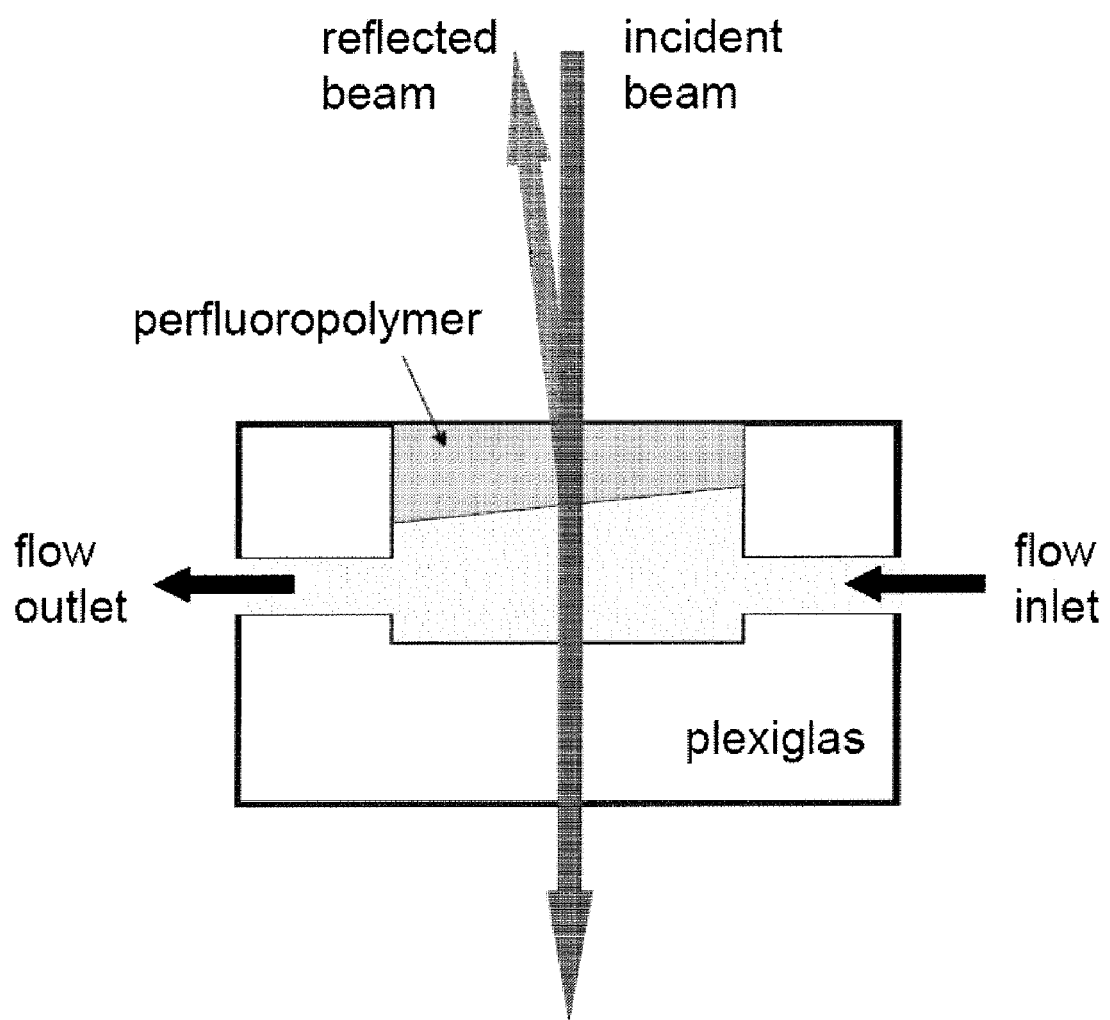
FIG. 3 illustrates a Plexiglas flow cell connected to a flow circuit as described in Example 4.

Measurement in a Flow Cell of the Presence in a Solution of Mouse IgG Antibodies by the Interaction with Anti-Mouse IgG Antibodies A flow cell with internal volume of about 100 mL has been obtained in a Plexiglas parallelepiped with sides 2 cm×2 cm×3 cm as in FIG. 3. A window of a copolymer of TFE containing 60% by moles of perfluorodioxole TTD is inserted in a side of the cell (grey element in FIG. 3). The internal surface of the window makes an angle of 5° with the external side. The cell is connected to a flow circuit by two pipes of diameter 1 mm.

A light beam coming from a 5 milliwatt laser He—Ne is impinging perpendicularly on the external side of the window of perfluoropolymer. The reflected light coming from the interface aqueous solution-perfluoropolymer, with a direction making an angle of around 5° with the normal to the external surface, is detected by an amplified photodiode converting the reflected light intensity into an electrical signal.

Step (a)

A 5 micromolar aqueous solution of mouse IgG antibody is flowed into the cell with a flow rate of 20 microliters/minute.

Figure 4:
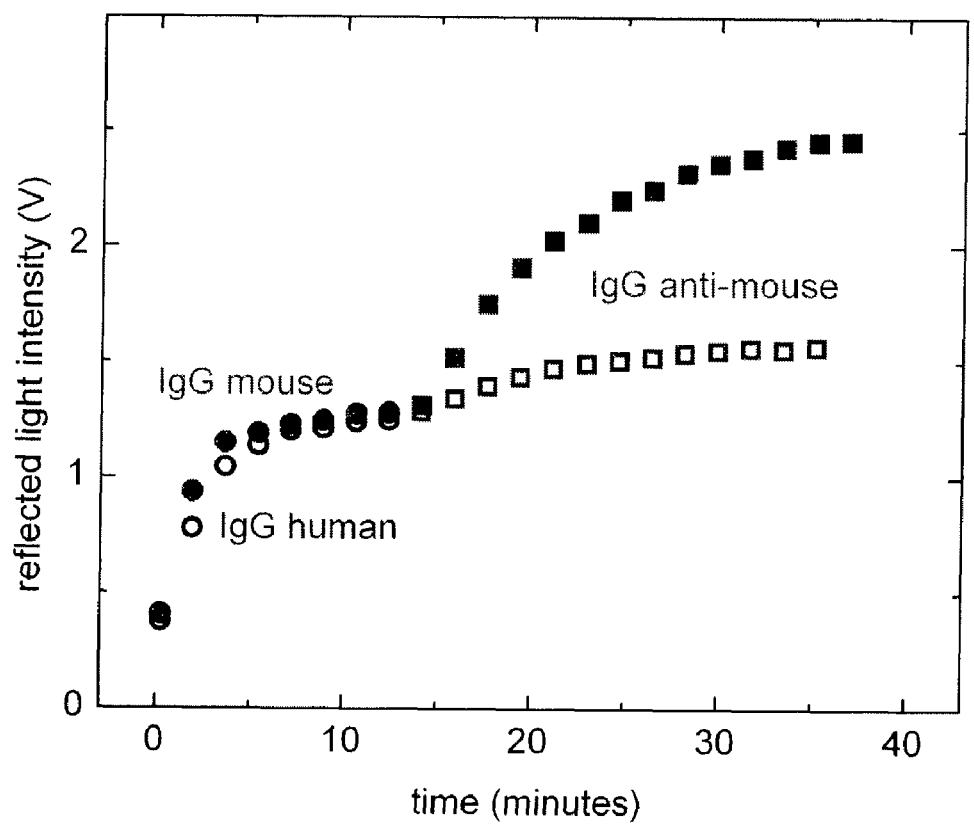
FIG. 4 is a graph depicting the intensity of reflected light (V) as a function of time (hours) of the solutions described in Examples 4 and 5.

During the flow, the intensity of the light reflected from the interface aqueous solution-perfluoropolymer is measured at intervals of 2 minutes. The measured values (filled dots in FIG. 4) are reported in a diagram as a function of time, obtaining the curve reported hereinafter.

The progressive covering of the window by the flowed antibody is observable from the variation of the light intensity measured by the photodiode.

The complete covering is clearly shown by the achievement of an asymptotic value of the measured light intensity.

Step (b)

After the achievement of an asymptotic value, a 5 micromolar aqueous solution of anti-mouse IgG antibody made in goat is flowed in the cell with a flow rate of 20 microliters/minute. The intensity of the reflected light is measured as in step (a) and the values are reported in a diagram as a function of time (filled squares in FIG. 4). After 20 minutes the intensity of the light nearly doubles the value measured at the end of step (a).

Example 5 (Comparative Example)

Control Experiment

Measurement in a Flow Cell of the Aspecific Interaction Between Human IgG Antibodies and Anti-Mouse IgG Antibodies The flow cell of the Example 4 is cleaned with a continuous flow for 3 hours of a unimolar aqueous solution of sodium idroxyde.

Step (a)

The procedure described in step (a) of Example 4 is repeated replacing the mouse IgG antibody with human IgG antibody. The light intensity is measured as in step (a) of Example 4 and the intensity values are reported in a diagram as a function of time (empty dots in FIG. 4.)

Step (b)

After the achievement of a constant value in the intensity of reflected light, the same procedure described in step (b) of Example 4 is repeated using the same 5 micromolar aqueous solution of anti-mouse IgG antibody made in goat. The intensity of the reflected light is measured as in step (b) of Example 4 and the values are reported in a diagram as a function of time (empty squares in FIG. 4). After 20 minutes the intensity of the light increases by about 20% compared to the value measured at the end of step (a). This increase is much lower than the one measured during the step (b) of Example 4 and is attributed to the aspecific interaction between anti-mouse IgG antibodies and the human IgG antibodies adsorbed on the surface during step (a).

Example 6

Figure 5:
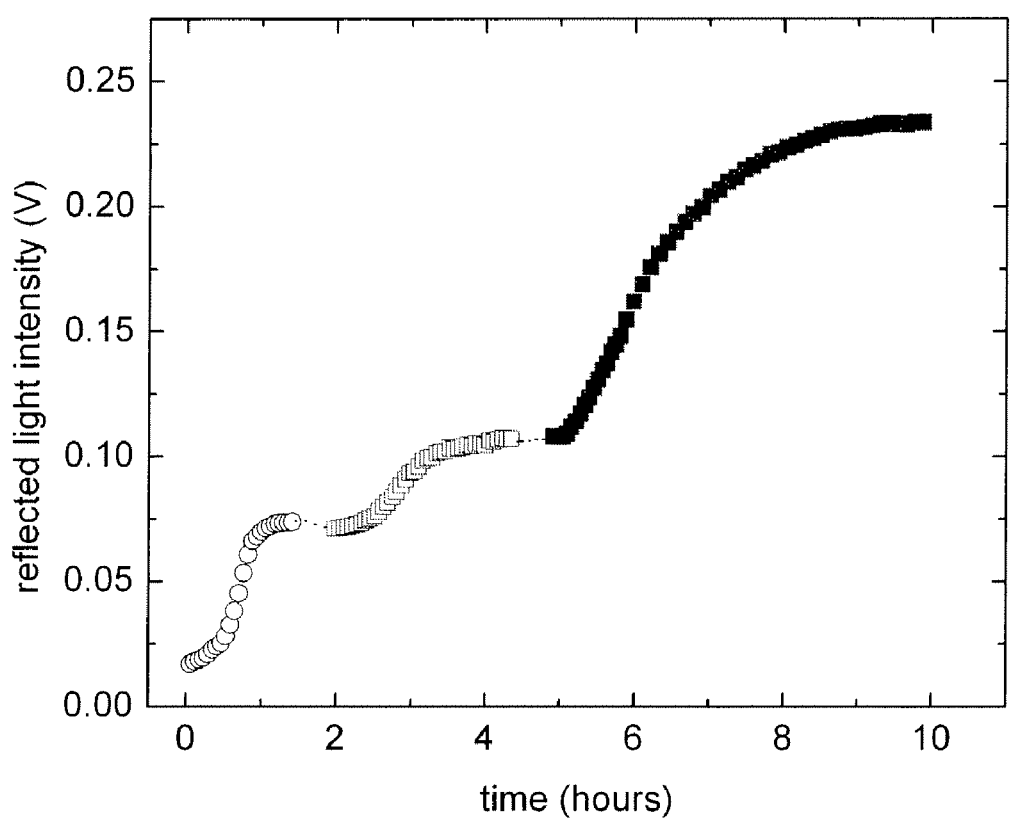
FIG. 5 is a graph depicting the intensity of reflected light (V) as a function of time (hours) of the solutions described in Example 6.

Measurement of the Interaction Between Human IgG Antibodies and Anti-Human IgG Antibodies Conjugated with Biotin and Immobilized by Avidin The flow cell described in Example 4, cleaned as described in Example 5, is filled with 100 microliters of water. 20 microliters of a 1.5 micromolar aqueous solution of Avidin are flowed in the cell. At the end of the addition, the intensity of the reflected light is measured as in the previous examples and the measured values are reported in a diagram as a function of time (empty dots of FIG. 5).

The complete covering of the perfluorpolymeric window by the Avidin is shown by the achievement of an asymptotic value of the measured light intensity.

When this asymptotic value is achieved, any residual content of Avidin not adsorbed on the surface is eliminated by a washing-out procedure consisting in flowing a 20 microliters/minute flow of water during 50 minutes. During the washing-out procedure, the reflected light intensity is measured and the values are reported in a diagram as a function of time (dotted line in FIG. 5).

After the washing-out procedure, 20 microliters of a 3 micromolar aqueous solution of anti-human IgG antibodies made in mouse conjugated with biotin are flowed into the cell. At the end of the addition, the intensity of the reflected light is measured as in the previous examples and the measured values are reported in a diagram as a function of time (empty squares of FIG. 5). The increase of the reflected light intensity is attributed to the interaction of the antibody conjugated with biotin with the Avidin adsorbed on the window surface.

When an asymptotic value is achieved, any residual content of antibody not interacting with the Avidin covering the surface is eliminated by a washing-out procedure consisting in flowing a 20 microliters/minute flow of water during 50 minutes. During the washing-out procedure, the reflected light intensity is measured and the values are reported in a diagram as a function of time (dotted line in FIG. 5).

After the washing-out procedure, 10 microliters of a 2 micromolar aqueous solution of human IgG antibodies are flowed into the cell. At the end of the addition, the intensity of the reflected light is measured as in the previous examples and the measured values are reported in a diagram as a function of time till the achievement of an asymptotic value (filled squares of FIG. 5).

The increase of the reflected light intensity is attributed to the interaction of the human IgG antibodies with the anti-human IgG antibodies covering the window surface.

The invention claimed is:

1. A method for determining the binding constant of interacting molecular species and of the concentration of a ligand in a solution comprising the step of:
   measuring the intensity of the light reflected by a flat surface comprising at least one perfluoropolymer, at least one receptor that is adsorbed to the surface of the perfluoropolymer or chemically bound to the surface of the perfluoropolymer, and at least one ligand molecule that interacts with the receptor by the steps of:
   contacting a surface of the perfluoropolymer with an aqueous solution containing from 1 nanogram/ml to 10 milligrams/ml of the receptor to form a first solution;
   optionally measuring the light intensity reflected from the interface between the aqueous solution of the receptor and the surface of the perfluoropolymer in the first solution; optionally contacting a surface of the perfluoropolymer with other aqueous or non-aqueous solutions of the receptor;
   adding a predetermined volume of an aqueous solution of a ligand having a predetermined concentration to the first solution to obtain a second solution, wherein the ligand concentration is $[T_O]$;
   repeating the adding of a predetermined volume of an aqueous solution of a ligand step;
   measuring after each adding of a predetermined volume of an aqueous solution of a ligand step the light intensity I reflected from the interface between the aqueous solution of the ligand and the surface of the perfluoropolymer in the second solution; and
   correlating the reflected light intensity data I as a function of the ligand concentration $[T_O]$ with formula (1):

$$I = cI_0(R^\perp \sin^2 v + R^\| \cos^2 v) + I_N \quad (1)$$

wherein
$I_0$ represents the incident light intensity on the interface,
c is a factor taking into account the surface roughness and is 1 only in case of a flat surface,
$I_N$ is the light intensity measured by the detector in the absence of the polymer,
v is the direction of the light polarization the incidence plane,
$R^\perp$ and $R^\|$ are the reflection coefficients drawn from the Fresnel formulas for a thin layer respectively in case of polarization perpendicular and parallel to the incidence plane, said $R^\perp$ and $R^\|$ being dependent on the ligand amount in contact with the receptors adsorbed on the interface from which the ligand concentration $[T_L]$ interacting with the receptors on the surface and optionally by means of Langmuir absorption formula, the K constant of receptor-ligand binding are obtained.

2. The method according to claim 1, wherein the receptor is selected from the group consisting of antibodies, proteic or peptidic complexes, nucleic acids, lipids, amphiphilic surfactants, or block polymers ended with a receptor,
   wherein the receptor is optionally mixed with other intercalating materials that do not have the receptor function.

3. The method according to claim 1, wherein in the correlating the reflected light intensity data I as a function of the ligand concentration $[T_O]$ step,
   the light incidence angle, v, is 45°,
   the polarization is perpendicular to the incidence plane (v=90°),
   the difference $\Delta n$ between the refractive indexes of the aqueous solution and of the polymeric substratum is lower than or equal to 0.012,
   the refractive index of the receptor is equal to the refractive index of the ligand,
   the thickness of the molecular layer of adsorbed or immobilized receptors and interacting ligands is lower than 15 nm, and
   the reflected intensity I is determined according to the following formula (2) approximated with an error lower than 1% with respect to the complete formula (1):

$$I = 2I_0\left(\frac{\pi V N_a}{\lambda A}\right)^2 \frac{(n_a^2 - n_0^2)(n_a^2 n_0^2 - n_0^4 + 2n_a^2 \Delta n)}{n_0^4}\left(\frac{m_R [T_R]}{\rho_R} + \frac{m_L [T_L]}{\rho_L}\right)^2 + I_b \quad (2)$$

wherein
$I_o$, $[T_L]$, $\Delta n$ are as above defined,
$[T_R]$ is the concentration of receptors absorbed or immobilized on the surface,
$n_a$ is the refractive index of the ligand and of the receptor,
$m_L$, $\rho_L$ represent the molecular weight and the density of the ligand respectively,
$m_R$, $\rho_R$ represent the molecular weight and the density of the receptor respectively,
V is the volume of the aqueous solution,
A is the area of the polymeric material surface on which the receptor and ligand interaction takes place,
$\lambda$ the wave length of the incident light,
$n_0$ is the refractive index of the aqueous solution, and $I_b$ the intensity measured before the contacting a surface of the perfluoropolymer with an aqueous solution containing from 1 nanogram/ml to 10 milligrams/ml of the receptor step receptor addition.

4. The method according to claim 3, wherein in the correlating the reflected light intensity data I as a function of the ligand concentration $[T_0]$ step, the concentration $[T_L]$ of ligand stuck on the surface in a state of thermodynamic equilibrium is expressed by the Langmuir absorption formula (3)

$$[T_L] = [T_0] + K^{-1} + [S_0] - \sqrt{([T_0] + K^{-1} + [S_0])^2 - 4[T_0][S_0]} \quad (3)$$

wherein $[T_0]$ is as above defined, $[S_0]$ is the molar concentration of receptor-ligand binding sites, and K is the affinity constant (also said binding constant).

5. The method according to claim 1, wherein the perfluoropolymer is a semicrystalline or amorphous polymer.

6. The method according to claim 1, wherein the perfluoropolymer is selected from the group consisting of:
   1) tetrafluoroethylene homopolymer (PTFE), or semicrystalline tetrafluoroethylene (TFE) copolymers;
   2) amorphous copolymers of TFE; and
   3) amorphous homopolymers of perfluorinated dioxole rings.

7. The method according to claim 6, wherein the perfluoropolymer is selected from the group consisting of:
   1) semicrystalline tetrafluoroethylene (TFE) copolymers containing from 0.5% up to about 10% by moles, the maximum limit being such that the copolymer is semicrystalline, of one or more comonomers selected from the group consisting of perfluoroalkylvinylethers (PAVE) perfluorodioxoles, and hexafluoropropene (HFP);
   2) amorphous copolymers of TFE with other fluorinated monomers selected from the group consisting of perfluoroalkylvinylethers (PAVE), perfluorodioxoles, hexafluoropropene (HFP), perfluorooxyalkylvinylethers, optionally containing "cure-site" monomers containing bromine or iodine atoms or iodine or bromine atoms in end position in the polymeric chain; and bisolefins having general formula:

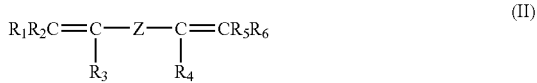

wherein:

$R_1$, $R_2$, $R_3$, $R_4$, $R_5$, $R_6$, equal to or different from each other, are H or $C_1$-$C_5$ alkyls, Z is a linear or branched $C_1$-$C_{18}$ alkylene or cycloalkylene radical, optionally containing oxygen atoms or a (per)fluoropoly-oxyalkylene radical; and 3) amorphous homopolymers of a perfluorodioxole of formula (I)

wherein Y is equal to F or to $OR_f$ wherein $R_f$ is a perfluoroalkyl having from 1 to 5 carbon atoms; $X_1$ and $X_2$, equal to or different from each other, are —F or —$CF_3$.

8. The method according to claim 7, wherein in class 2) as comonomer of TFE, diene monomers containing oxygen atoms which cyclize during the polymerization are used.

9. The method according to claim 8, wherein the diene monomers are selected from the group consisting of:

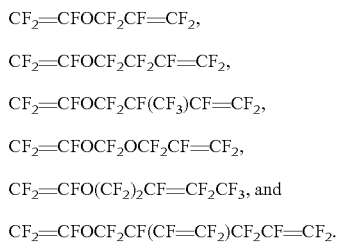

10. The method according to claim 7, wherein the perfluoropolymer is selected from those of classes 2) and 3).

11. The method according to claim 7, wherein the perfluoropolymer is a TFE copolymer containing from 20% to 60% by moles of 2,2,4-trifluoro-5-trifluoromethoxy-1,3-dioxole (TTD).

12. The method according to claim 7, wherein the perfluoropolymer is an amorphous copolymer of TFE of class 2) with a perfluorodioxole of formula (I)

13. The method according to claim 7, wherein the perfluoropolymer is an amorphous copolymer of TFE of class 2) with from 20% to 80% by moles of a perfluorodioxole of formula (I)

* * * * *